United States Patent [19]
Shetty et al.

[11] Patent Number: 5,326,362
[45] Date of Patent: Jul. 5, 1994

[54] METHOD OF SURFACE HARDENING ORTHOPEDIC IMPLANT DEVICES

[75] Inventors: H. Ravindranath Shetty; Walter H. Ottersberg, both of Warsaw; Jack E. Parr, North Webster; Roy D. Crowninshield, Warsaw, all of Ind.

[73] Assignee: Zimmer, Inc., Warsaw, Ind.

[21] Appl. No.: 12,617

[22] Filed: Feb. 2, 1993

Related U.S. Application Data

[63] Continuation of Ser. No. 609,269, Nov. 5, 1990, abandoned.

[51] Int. Cl.$^5$ ............................ A61F 2/02; A01N 1/02
[52] U.S. Cl. ........................................ 623/66; 427/250
[58] Field of Search ..................... 623/16, 18, 11, 66, 623/20, 22, 23; 427/2, 250

[56] References Cited

U.S. PATENT DOCUMENTS

| | | | |
|---|---|---|---|
| 3,643,658 | 2/1972 | Steinemenan | 128/92 D |
| 4,040,129 | 8/1977 | Steinemann et al. | 3/1.9 |
| 4,687,487 | 8/1987 | Hintermann | 623/18 |
| 4,693,760 | 9/1987 | Sioshansi | 148/4 |
| 4,768,757 | 9/1988 | Nakamura et al. | 266/252 |
| 4,790,851 | 12/1988 | Suire et al. | 623/16 |
| 4,855,101 | 8/1989 | Mohs et al. | 419/8 |

FOREIGN PATENT DOCUMENTS

| | | |
|---|---|---|
| 918500679 | 3/1991 | European Pat. Off. |
| 2123207 | 1/1971 | France . |
| 63-241157 | 3/1988 | Japan . |
| 585278 | 7/1977 | Switzerland . |
| 83-775335/39 | 4/1981 | U.S.S.R. |
| 2154450 | 9/1985 | United Kingdom . |

OTHER PUBLICATIONS

Nuclear Instruments & Methods in Physics Research, vol. B1920, No. P1, Feb. 1987, Amsterdam-NL, pp. 204-208; P. Sioshansi-Medical Applications of Ion Beam Processes.

"Titanium" by A. D. McQuillan and M. K. McQuillan, Metallury of Rare Metals, vol. 14, 1956, pp. 412-427.

Novikova, "Nitriding of Titanium Alloys at High Pressures", Physical Mettalurgy of Titanium, 1964, pp. 166-174.

Frantsevich et al, "Nitriding of Titanium in Rarefied Activated Nitrogen", Institute of Materials Science, Academy of Sciences of the Ukrainian SSR. Translated from Poroshkovaya Metallurgiya, No. 12(276), pp. 30-33, Dec., 1985.

Rolinski, "Effect of Nitriding on the Surface Structure of Titanium", Journal of the Less-Common Metals, 141 (1988), pp. L-11-L-14.

Strafford et al, "The Interaction of Titanium and Titanium Alloys with Nitrogen at Elevated Temperatures. I. The Kinetics and Mechanism of the Titanium-Nitrogen Reaction", Oxidation of Metals, vol. 10, No. 1, 1976, pp. 41-67.

Katayama et al "Surface Hardening of Titanium by Laser Nitriding", Laser Processing Materials, Los Angeles, Calif., Feb. 26-Mar. 1, 1984, pp. 159-166.

Matsimovich et al "Structure Formation in Nitrided Layers of Titanium Alloys", Met Sci Heat Treat (USSR), vol. 28, Issue No. 5-6, May-Jun. 1986, pp. 393-397.

(List continued on next page.)

*Primary Examiner*—David Isabella
*Attorney, Agent, or Firm*—Baker & Daniels

[57] ABSTRACT

A method of surface hardening titanium orthopedic implant devices, and a titanium orthopedic implant device prepared by the disclosed method. An orthopedic implant device made of pure titanium or a titanium alloy, such as Ti-6Al-4V (ELI) is exposed to molecular nitrogen gas at a process temperature and for a process time duration sufficient to enhance surface hardness and wear resistance properties, without the formation of a measurable TiN layer that tends to increase surface roughness and diminish wear resistance properties. The process temperature is in the range of 750° F. to 1300° F., preferably about 1100° F. and the process time duration at the preferred process temperature is approximately 8 hours. The hardened surface of the titanium implant occurs primarily due to solid solution hardening of the titanium with nitrogen by dissolution.

18 Claims, 2 Drawing Sheets

OTHER PUBLICATIONS

Matsimovich et al, "Nitriding of Titanium Alloys at the Atmospheric Pressure of Nitrogen", translated from Fiziko-Khimicheskaya Mekhanika Materialov, vol. 23, No. 6, pp. 36–39, Nov.–Dec., 1987.

Pivin et al, "Transmission Electron Microscopy Investigation of the Structural Transformations in Titanium or TiAl Implanted with Nitrogen, Carbon, Oxygen and Boron", Materials Science and Engineering, A115 (1989), pp. 83–88.

Mitchell et al, "Surface Treatments for Improving the Wear-Resistance and Friction Properties of Titanium and Its Alloys", Journal of the Institute of Metals, 1964–65, vol. 93, pp. 301–386.

Cuthill et al, "Nitriding Phenomena in Titanium and the 6Al–4V Titanium Alloy", Journal of Research of the National Bureau of Standards, A. Physics and Chemistry, vol. 64A, No. 1, Jan.–Feb. 1960.

Raveh et al, "Microstructure of Low Temperature RF Plasma Nitrided Titanium Alloy", Israel J. Technol, vol. 24, 1988, pp. 489–497.

Braganza et al, "Interaction of Nitrided Titanium With a Hydrogen Plasma", Journal of Nuclear Materials, vol. 87, 1979, pp. 331–340.

Rolinski, "Mechanism of High-Temperature Plasma Nitriding of Titanium", Materials Science and Engineering, vol. 100, 1988, pp. 193–199.

Rolinski, "Surface Properties of Plasma-Nitrided Titanium Alloys", Materials Science and Engineering, vol. A108, 1989, pp. 37–44.

Shibutami et al, "Nitriding of Titanium in Microwave Discharges", Journal of the Less-Common Metals, vol. 113, Nov. 15, 1985, pp. 177–187.

Avni, "Nitriding of Titanium and Its Alloys by $N_2$, $NH_3$, or Mixtures of $N_2+H_2$ in a dc Arc Plasma at Low Pressures ($\leq 10$ torr)", NASA Technical Memorandum 83803, Nov. 1984.

Rolinski, "Wear Resistance and Corrosion Behaviour of Plasma Nitrided Titanium Alloys", International Seminar on Plasma Heat Treatment: Sciente and Technology, Senlis, France, 21–23, Sep. 1987, pp. 255–263.

Matsumoto, "Nitriding of Titanium in a Radiofrequency Discharge III: Interation of Hydrogen Plasma and Nitrided Titanium", Journal of the Less-Common Metals, vol. 107, May 15, 1985, pp. 259–265.

Matsumoto et al, "Metal Nitride Film Formation in Plasmas", Advances in Low-Temperature Plasma Chemistry, Technology, Applications, vol. I, 1984, pp. 53–79.

Korhonen, "Plasma Nitriding at Low Pressures", 2nd International Congress on Heat Treatment of Materials: 1st National Conference on Metallurgical Coatings, Florence, Italy, Sep. 1982, pp. 333–340.

Konuma et al, "Nitriding of Titanium in a Radio Frequency Discharge", Journal of the Less-Common Metals, vol. 52, Mar. 1977, pp. 145–152.

Rolinski et al, "Metallographic and Radioisotopic Investigation of the Plasma Nitrided $Ti_6Al_{2.5}Mo_2Cr$ Alloy with AN $\alpha+\beta$", Journal of the Less-Common Metals, vol. 136, Dec. 1987, pp. 135–145.

Li et al, Study on the Deposited Titanium Nitride Layer by Plasma Chemical Vapor Deposition, Heat Treat Metal, Issue No. 11, 1987, pp. 3–8.

Badini et al, "Texture of Surface Layers Obtained by Ion Nitriding of Titanium Alloys".

Deutchman et al, "Ion Nitriding and Nitrogen Ion Implantation: Process Characteristics and Comparisons", BeamAlloy Corporation, Dublin, Ohio.

Badini et al, "Characterization of Surface Layers in Ion-Nitrided Titanium and Titanium Alloys", Journal of the Less-Common Metals, vol. 143, Oct. 1988, pp. 129–141.

Tesi et al, "Ion-Nitriding Techniques for Titanium and Titanium Alloys", Heat Treatment '87, London, May 1987, pp. 45–53.

Metin et al, "Kinetics of Layer Growth and Multiphase Diffusion in Ion-Nitrided Titanium", Metallurgical Transactions A, vol. 20A, Sep. 1989, pp. 1819–1832.

Kembaiyan et al, "Ion Nitriding of Titanium and Ti–6Al–4V Alloy", Department of Materials Engineering, Drexel University, pp. 119–129.

Raveh et al, "Characteristics of R. F. Plasma Nitrided Titanium Alloys", Surface and Coatings Technology, vol. 36, Dec. 1988, pp. 183–190.

Grill, "Ion Beam Nitriding of Titanium and Titanium Alloy", Vacuum, vol. 33, No. 6, 1987, pp. 333–337.

Coll et al, "Surface Modification of Medical Implants and Surgical Devices Using TiN Layers", Surface and Coatings Technology, vol. 36, 1988, pp. 867–878.

(List continued on next page.)

OTHER PUBLICATIONS

Martinella et al, "Wear Behavior and Structural Characterization of a Nitrogen Implanted Ti6Al4V Alloy at Different Temperatures", Ion Implantation and Ion Bean Processing of Materials, Boston, Mass., Nov. 14-17, 1983, pp. 711-716.

Rie et al, "Thermochemical Surface Treatment of Titanium and Titanium Alloy Ti-6Al-4V by Low Energy Nitrogen Ion Bombardment", Materials Science and Engineering, vol. 69, 1985, pp. 473-481.

Martinella et al, "Wear Behaviour of Nitrogen-Implanted and Nitrided Ti-6Al-4V Alloy", Materials Science and Engineering, vo. 69, 1985, pp. 247-252.

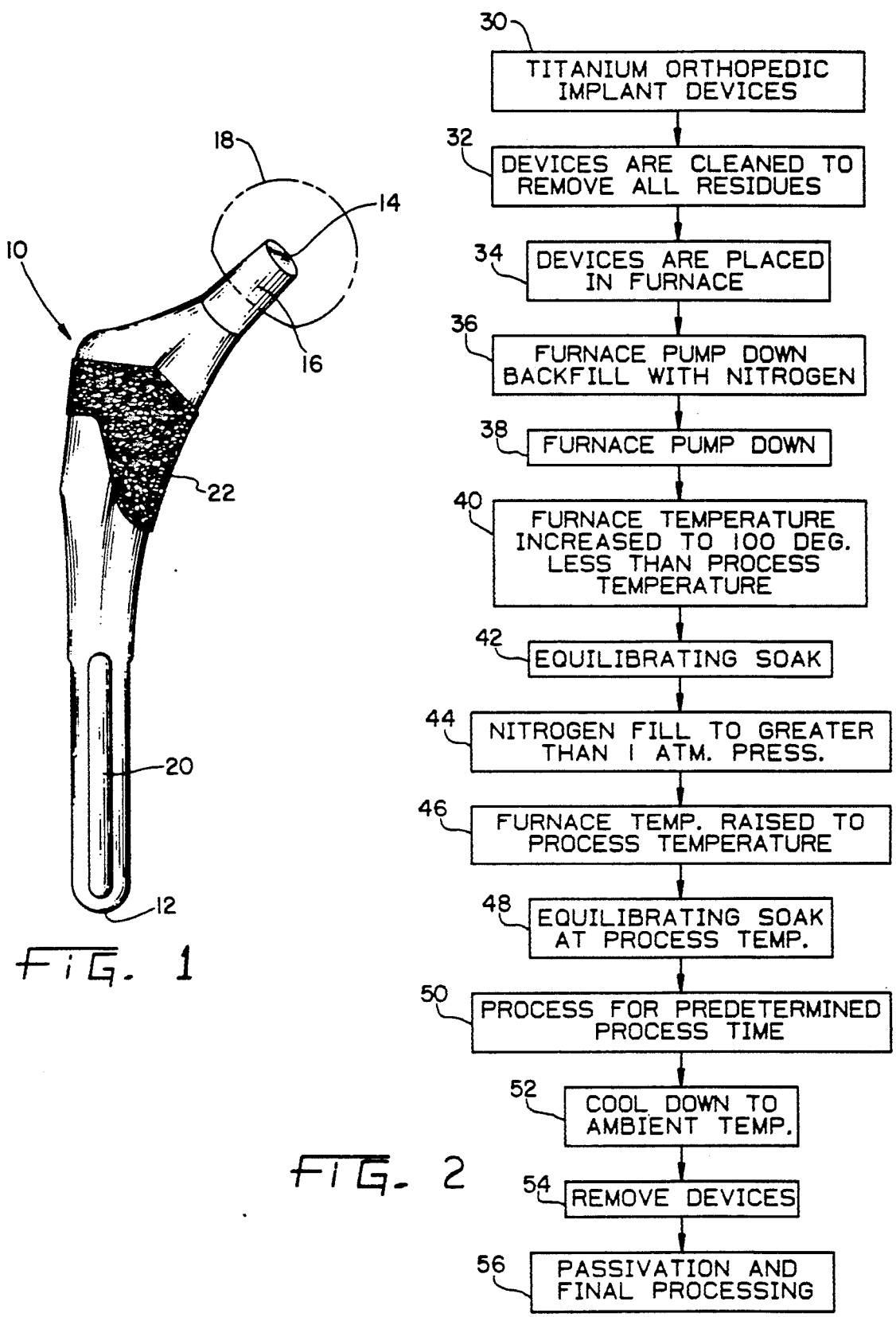

METHOD OF SURFACE HARDENING ORTHOPEDIC IMPLANT DEVICES

This is a continuation of application Ser. No. 07/609,269, filed Nov. 5, 1990, now abandoned.

BACKGROUND OF THE INVENTION

The present invention relates generally to titanium orthopedic implant devices and, more particularly, to a surface hardening process applicable to such devices, wherein surface hardness and wear resistance properties of the implant are enhanced with minimal loss in fatigue strength.

Commercially pure titanium and titanium alloys are used for orthopedic applications because of their strength, corrosion resistance, and biocompatibility. However, the tribological behavior of titanium and its alloys is characterized by a high coefficient of friction and poor wear performance, resulting in a tendency for titanium and its alloys to seize or gall under conditions of wear. Therefore, in those orthopedic applications requiring enhanced wear resistance properties, the surface of a titanium implant must be hardened. In the past, surface hardening of orthopedic implants has been achieved either by depositing a nitride coating on the surface of an implant, or by forming a layer of titanium nitride (TiN) on the surface of a titanium substrate.

A TiN layer is produced on the surface of a titanium implant by various nitriding methods, including gas nitriding, chemical salt bath nitriding, plasma or ion nitriding, and ion implantation. Of these alternatives, gas nitriding is believed to be the earliest method used for hardening titanium, and still exhibits advantages over the other methods in terms of cost and ease of manufacture. For instance, gas nitriding permits efficient batch processing of many parts concurrently in a furnace chamber; whereas, the plasma nitriding and ion implantation methods require line-of-sight bombardment of the workpiece, thereby limiting the number of parts that may be processed concurrently.

Gas nitriding of titanium and its alloys has historically been performed at elevated temperatures in the range of 700° C. to 200° C. (1292° F. to 2192° F.) U.S. Pat. No. 4,768,757 discloses a method for nitriding the surface of a titanium dental cast, wherein it is stated that the temperature generally used for the nitriding treatment falls in the range of 700° C. to 880° C. because nitriding generally begins to proceed in the neighborhood of 700° C. and the heat distortion or phase transition point of titanium is about 882° C. Characteristic of virtually all gas nitriding processes is the formation of a relatively thick TiN layer on the surface of the titanium, caused by a scaling reaction. Essentially, successful nitriding of a titanium orthopedic implant for the purpose of providing a hardened surface is defined by the observance of a distinct and measurable TiN layer achieved by elevated temperatures, as taught by the prior art.

It has now been discovered that the aforementioned gas nitriding process, as applied to a titanium orthopedic implant device, may produce several undesirable changes in the physical and mechanical properties of the device. Notwithstanding increases in overall surface hardness, the TiN layer formed on the surface of the device by gas nitriding at elevated temperatures tends to be brittle and exhibits increased surface roughness, both of which cause losses in the fatigue strength of the implant. Also, temperature induced changes in the dimensions of the titanium orthopedic implant device may occur.

Potential losses in the fatigue strength and increases in the surface roughness of a titanium orthopedic implant device are of particular concern in orthopedic applications involving load bearing prostheses in articulating contact with bone or polymers. For instance, under conditions of sliding or articulation of the nitrided implant against other surfaces, particularly bone and polymers, the increased surface roughness may produce wear debris that can act as an abrasive medium. Consequently, it is desirable to reduce the possibility of wear debris and its potential impact on the stability of orthopedic implants by enhancing the surface hardness of the titanium material without substantial losses in fatigue strength or wear resistance properties.

SUMMARY OF THE INVENTION

Generally, the present invention provides a process for surface hardening an orthopedic implant device made of pure titanium or a titanium alloy, wherein the surface hardness of the device is enhanced while maintaining wear resistance and fatigue strength. The invention also encompasses orthopedic implant devices in accordance with the claimed process.

Generally, the process of the present invention enhances the surface hardness of the titanium implant device by thermal reaction of nitrogen gas at low temperatures. Consequently, surface hardness and wear properties are enhanced with minimal loss in fatigue strength. More specifically, the use of a low process temperature prevents the formation of a measurable TiN layer on the surface that tends to increase surface roughness and diminish wear resistance properties in orthopedic implant applications involving articulating joint surfaces.

An advantage of the surface hardening method of the present invention is that the surface of an orthopedic implant device made of titanium is hardened without substantially affecting the mechanical and physical properties of the material.

Another advantage of the surface hardening method of the present invention is that the method is particularly adapted for use on load bearing prostheses that contact with bone or polymers, due to a significant improvement in wear resistance coupled with a minimal loss in fatigue strength.

A further advantage of the surface hardening method of the present invention is that it permits batch processing of orthopedic implant devices, as opposed to individual processing by prior art plasma nitriding processes requiring a "line of sight" to the parts for ion bombardment.

Yet another advantage of the surface hardening method of the present invention is that formation of a TiN layer and its attendant surface roughness is substantially eliminated by the use of a relatively low process temperature, thereby improving wear resistance properties of the treated surface.

The invention, in one form thereof, provides a method of manufacturing an orthopedic implant device having enhanced surface hardness and wear resistance properties. The method includes several essential steps, including an initial step of providing a titanium substrate in the form of an orthopedic implant device, or component thereof. A surface hardening step is then performed. Specifically, the surface of the titanium substrate is hardened by exposure to an atmosphere of molecular nitrogen gas at a process temperature within the range of 750° F. to 1300° F. for a process time duration sufficient to achieve a hardened surface region characterized primarily by solid solution hardening of the surface by dissolution of nitrogen in the titanium substrate.

The invention further provides, in one form thereof, an orthopedic implant device having enhanced surface hardness and wear resistance properties, prepared by a process including a first step of providing a substrate of titanium material in the form of an orthopedic implant device. The substrate is then exposed to an atmosphere of molecular nitrogen gas at a process temperature within the range of 750° F. to 1300° F. for a process time duration beyond which wear resistance properties of the substrate begin to decrease due to surface roughness. In one aspect of the invention, the process temperature is approximately 1100° F. and the process time duration is approximately eight hours.

BRIEF DESCRIPTION OF THE DRAWINGS

FIG. 1 is a side view of a femoral component for a hip prosthesis, representing a titanium orthopedic implant device of the type to which the surface hardening process of the present invention is applicable;

FIG. 2 is a diagrammatic representation of the process steps involved in an exemplary embodiment of the method of the present invention.

DESCRIPTION OF THE PREFERRED EMBODIMENT

Figure 3:
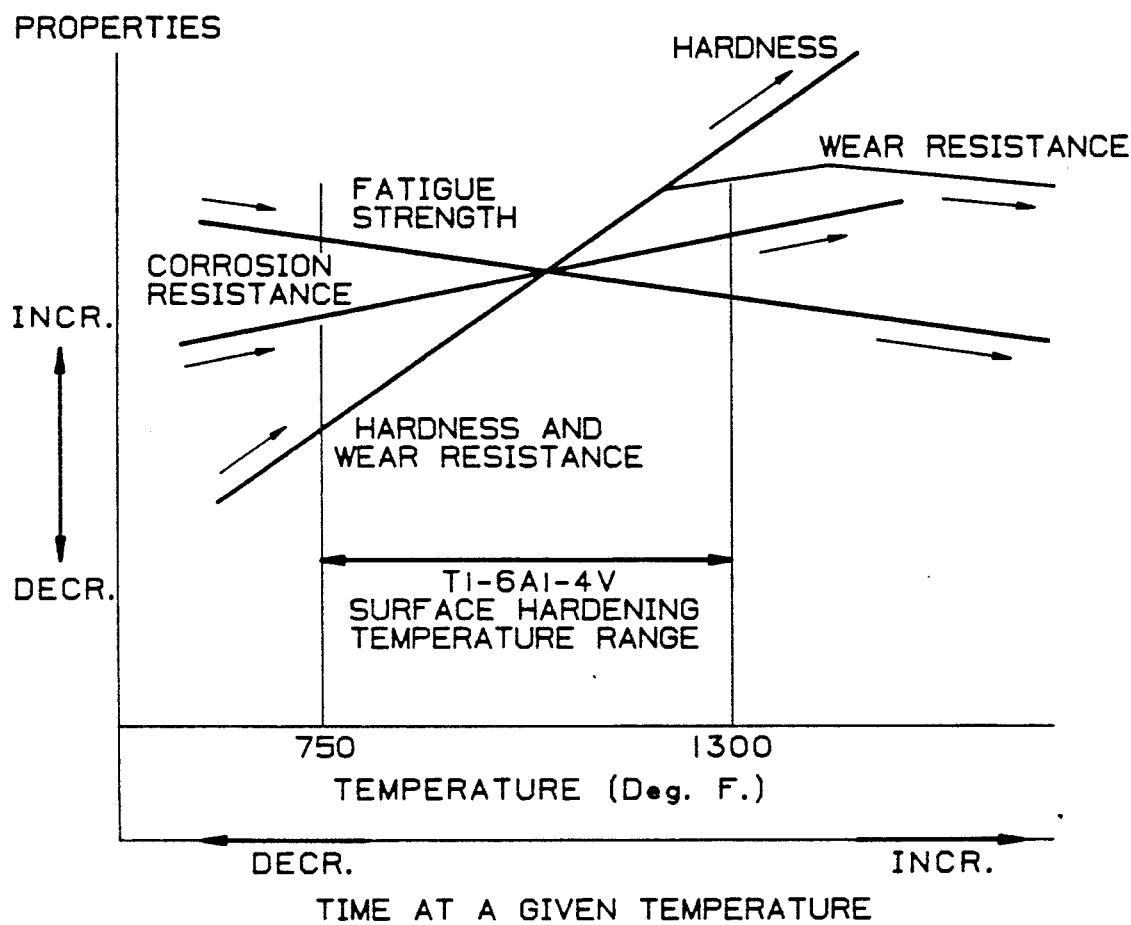
FIG. 3 is a graph diagram showing the qualitative relationship between process temperature and time and physical properties of titanium orthopedic implant devices subjected to the surface hardening process of the present invention.

Referring now to FIG. 1, there is shown an orthopedic implant device 10 fabricated from a titanium material and treated in accordance with the surface hardening method of the present invention. The phrase "titanium material" as used herein is intended to encompasses both commercially pure titanium (CP-Titanium) and the alloys based on titanium. One such titanium alloy commonly used in orthopedics applications because of its strength, corrosion resistance, and biocompatibility is Ti-6Al-4V (ELI—extra low interstitial), based on titanium, aluminum, and vanadium.

In the disclosed embodiment of the present invention, orthopedic implant device 10 comprises a femoral component for a hip prosthesis of the type disclosed in U.S. Pat. No. 4,813,963, assigned to the same assignee as the present invention, the disclosure of which is hereby incorporated by reference. Generally, femoral component 10 includes a distal end 12, and a proximal end 14 having a neck 16 adapted to carry a ball 18 shown in phantom in FIG. 1. Femoral component 10 is intended to fit within an intramedullary canal of a femur (not shown) such that proximal end 14 extends outwardly from the intramedullary canal of the femur to cooperate with an acetabulum by means of ball 18. Femoral component 10 includes a plurality of longitudinally extending grooves 20 at distal end 12 and a porous surface 22 encircling the femoral component at an intermediate location along femoral component 10.

Referring now to FIG. 2, the steps for hardening the surface of a stainless steel orthopedic implant device in accord with an exemplary embodiment of the present invention are diagrammatically illustrated. Generally, block 30 represents the first step of providing at least one titanium orthopedic implant device or component part thereof, i.e., a substrate of titanium material. As previously discussed, Ti-6Al-4V (ELI) alloy is used for the implant device in the disclosed embodiment of the invention. Block 32 represents the next step of cleaning the devices to remove all residues. Specifically, after an initial cleaning, the orthopedic implant devices are handled with gloved hands. The devices are then ultrasonically cleaned for thirty (30) minutes in Isopropyl Alcohol, and are then spray-dried with Freon.

The next step of the process, represented by block 36, is placing the implant devices in a furnace. The furnace of the preferred embodiment is a vacuum furnace manufactured by Vacuum Furnace Systems (VFS) Corporation of Souderton, Pa. It is recommended that any furnace used for surface hardening an orthopedic implant device of Ti-6Al-4V (ELI) titanium alloy be capable of maintaining a pressure level of $1 \times 10^{-6}$ Torr, a leak rate not exceeding five microns per hour, and a thermal uniformity within ±25° F. in vacuum and within ±50° F. in a nitrogen gas atmosphere, at operating temperatures.

As part of the step of placing the implant devices in the furnace, a furnace load is prepared, consisting of properly cleaned and passivated orthopedic implant devices assembled on suitable fixtures. The implant devices may or may not include any preattached titanium bone ingrowth features. When placed in the furnace, the boundaries of the load must not extend beyond the uniform hot zone of the furnace. The number of parts in a load is dependent upon component size and fixture geometry. If desired, a predetermined mass of compacted titanium wire may be equally divided and placed within and around the load to act as a getter. Only materials that do not contaminate Ti-6Al-4V (ELI) alloy and CP-Titanium may be placed in the furnace with the load. Examples include outgassed high purity graphite, high purity alumina, molybdenum, tantalum, and titanium.

After the load is placed in the furnace chamber, the next step is pumping down (evacuating) the chamber to $1 \times 10^{-5}$ Torr pressure and then backfilling with high purity nitrogen gas to one atmosphere (or 0 psig), as represented by block 36. The step of block 36 is preferably performed at least twice, in order to remove any impurities. The chamber is then purged by once again pumping down or evacuating to $1 \times 10^{-5}$ Torr pressure, as represented by block 38. The minimum purity of the molecular nitrogen gas used in the disclosed embodiment of the present invention is preferably 99.998 percent, with maximum allowable impurities of 10 ppm oxygen and 4 ppm water (vapor). In addition to these allowable impurities, the nitrogen gas may contain a trace of argon. The nitrogen gas is undiluted non-rarefied. The gas should also have a −90° F. dew point.

The next step, as represented by block 40 in FIG. 2, is heating the furnace at a rate of 25° F. per minute to a temperature of 1000° F. ±50° F. Block 42 represents the next step of holding that temperature for 30 minutes to accomplish an equilibrating soak. The next step, represented by block 44, is filling the furnace with nitrogen gas to a pressure greater than 1 atmosphere pressure, e.g., 1 psi above 1 atmosphere. A preferred range for the attained pressure is a minimum of 1 psig and a maximum of 2 psig; however, process pressure may be varied further without departing from the spirit or scope of the invention. Block 46 of FIG. 2 represents the next step of heating the furnace at 20° F. per minute to a process temperature of 1050° F. ±50° F. In one embodiment, a process temperature of 1100° F. is used. In the next step of the process, as described in block 48, an equilibrating soak is performed for 30 minutes at the process temperature.

According to the next step of the process, represented by block 50, the implant devices are processed for a predetermined process time duration at the process temperature. Specifically, a surface hardening cycle is run at the process temperature for not less than 8 hours or more than 8 hours, 15 minutes at a process temperature of approximately 1100° F. Incidentally, the surface hardening cycle is not considered to begin until any and all monitoring thermocouples are within the specified range for the process temperature.

Upon completion of the surface hardening cycle, the load may be either nitrogen quenched or furnace cooled, as the implant devices are cooled down, according to the step of block 52. The furnace is not opened until the temperature of the load is stabilized at 200° F. ±25° F., or less, as measured by the highest reading monitoring thermocouple. The furnace may then be opened and the load removed, after which final passivation and processing is performed according to the step of blocks 54 and 56, respectively.

While a specific combination of process temperature and time have been specified, it is appreciated that the titanium surface hardening method of the present invention can also be conducted at different temperatures in the range of 750° F. to 1300° F. for different time periods sufficient to produce the characteristic results of the present invention. This is graphically illustrated by the graph diagram of FIG. 3 showing the qualitative relationship between process temperature and time and the physical properties of titanium orthopedic implant devices subjected to the surface hardening process of the present invention.

Referring to FIG. 3, it can be seen that surface hardness and wear resistance of Ti-6Al-4V increase with increasing process temperature within the range of 750° F. to 1300° F., in accordance with the surface hardening process of the present invention. However, beyond this temperature range the formation of a measurable TiN layer on the surface increases surface roughness, as previously described, causing wear resistance to diminish. Fatigue strength exhibits a gradual degradation with increasing process temperature, while corrosion resistance shows a slight improvement. Similarly, the aforementioned changes in the physical properties are generally observed as process time is varied for a given process temperature within the specified temperature range.

In order to monitor the process, witness coupons of the same alloy and condition as the items in the load are placed in the furnace to assess the outcome of the process. One coupon is placed as closely as possible to the center of the load. The remaining coupons are placed in the hottest and coldest spots in the load as defined by previous survey. After the completion of the surface hardening cycle, the microhardness of the treated coupons is measured with a 2 gram load using a Knoop indentor. The surface hardening process of the present invention has been found to significantly increase the surface hardness of the titanium material from its untreated condition. For instance, the 2 gram Knoop surface hardness of Ti-6Al-4V (ELI) alloy processed at a process temperature of 1050° F. ±50° F. for a process time of 8 hours is approximately 2000 KHN, while the 2 gram Knoop surface hardness of the untreated alloy is in the range of 300–600 KHN.

Nitrogen depth profiles are also performed on the coupons to measure the depth concentration of nitrogen and oxygen, as by Electron Spectroscopy for Chemical Analysis (ESCA). The peak nitrogen concentration falls within the range of 10 atomic percent to 50 atomic percent, and occurs at a depth between 100 and 1000 Angstroms below the surface.

The fatigue strength of titanium alloy Ti-6Al-4V (ELI) subjected to the process of the present invention was quantitatively tested by measuring the bending fatigue or flucture of a rotating beam in units of kilopounds/in$^2$. It was determined that the disclosed low temperature surface hardening process results in a minimum loss of fatigue properties. Specifically, among the tested samples, the measured loss in fatigue strength was less than 10 percent and, more typically, less than 5 percent.

The wear resistance of titanium alloy Ti-6Al-4V (ELI) surface hardened in accordance with the disclosed process was tested by performing wear tests on a pin-on-disk wear tester, using ultrahigh molecular weight polyethylene (UHMWPE), bone, and bone cement pins to simulate actual implant conditions. Significant improvement in both sliding and abrasive wear resistance properties were observed. In contrast, it was discovered that prior art gas nitriding at elevated temperatures produces a layer of TiN that increases surface roughness, i.e., an irregular "pointed" surface finish. Consequently, when articulating contact is made with the smooth surface of a bone or polymer, TiN scales break off of the rough surface and act as an abrasive medium.

Concerning the corrosion resistance properties of titanium subjected to the surface hardening process of the present invention, there does not appear to be any compromise of the corrosion resistance. In fact, it has been found that surface hardened titanium and titanium alloys exhibit better corrosion resistance than untreated titanium and titanium alloys.

In an effort to analyze the nature of the hardened surface produced by the aforementioned method of the present invention, treated samples of polished Ti-6Al-4V (ELI) were analyzed through Secondary Ion Mass Spectroscopy (SIMS), Ion Scattering Spectroscopy (ISS), x-ray diffraction, and Electron Spectroscopy for Chemical Analysis (ESCA) to identify phases or species present on the surface. For example, the SIMS analysis used Ar40+ at 2000 ev to sputter to a depth of about 600 Angstroms, thereby analyzing surface chemistry versus depth into the samples and producing a depth profile including various spectra.

The surface hardening process of the disclosed preferred embodiment, as analyzed by the aforementioned methods, produces a hardened Surface layer, which is limited in thickness to a depth of approximately 0.20 μm (2000 Å). The hardened surface layer is believed to include titanium nitride ($Ti_xN_y$) with different stoichiometry, including $Ti_2N$, $Ti_2N_2$ (possibly as the compound TIN), $Ti_2NO$, $Ti_2NC$, etc. It is also believed to have $Ti_xO_y$ with different stoichiometry, including $TiO_2$, $Ti_2O$, $Ti_2O_3$, TiO, $Ti_2O_2$, etch. The hardened surface layer is also believed to have some carbides in the form $Ti_xC_y$, including TiC, $Ti_2C$, $Ti_2CO$, etc.

Underneath the hardened surface layer is a hardened diffusion region that is hardened due to solid solution hardening of the titanium alloy. The solid solution hardening elements in this case are nitrogen, oxygen, and carbon. This region extends several microns from the surface of the device. The SIMS and ISS analyses indicate that the hardened surface layer and hardened diffusion region together constitute the desired hardened surface. Specifically, metallurgical changes on the surface of the treated titanium implant device include the presence of titanium nitride ($Ti_2N$), titanium oxide, titanium carbide, and solid solution of nitrogen in titanium, all of which together produce the desired hardening effect.

While the surface hardening process of the present invention is particularly applicable to orthopedic applications involving load bearing prostheses in articulating contact with bone or polymers, e.g., hip, knee, ankle, elbow, shoulder, wrist, finger, and toe joints, it may also be used to treat all titanium and titanium alloy fracture fixation devices as well.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. A method of manufacturing a titanium orthopedic implant device having enhanced surface hardness and wear resistance properties, comprising the steps of:
   providing a titanium substrate in the form of an orthopedic implant device; and
   hardening the surface of said titanium substrate by exposing said titanium substrate to an atmosphere of undiluted molecular nitrogen gas at a process temperature within the range of 750° F. to 1300° F. for a process time duration sufficient to achieve a hardened surface region characterized primarily by solid solution hardening of the surface of the titanium substrate by dissolution of nitrogen in said titanium substrate.

2. The method of claim 1 in which said titanium substrate comprises commercially pure titanium (CP-Titanium).

3. The method of claim 1 in which said titanium substrate comprises a titanium alloy.

4. The method of claim 3 in which said titanium alloy is Ti-6Al-4V (ELI).

5. The method of claim 1 in which said process temperature is approximately 1100° F. and said process time is approximately eight hours.

6. The method of claim 1 in which said hardened surface region exhibits a peak nitrogen concentration within the range of 10 atomic percent to 50 atomic percent at a depth between 0.01 and 0.10 μm (100 and 1000 Å) below the surface of said titanium substrate.

7. The method of claim 1 in which said hardened surface region includes a hardened surface layer limited in thickness to a depth of approximately 0.20 μm (2000 Å) and a hardened diffusion region underneath said hardened surface layer, said surface layer comprising titanium nitride ($Ti_xN_y$), titanium oxide ($Ti_xO_y$), and titanium carbide ($Ti_xC_y$), and said hardened diffusion region comprising a solid solution of nitrogen, oxygen, and carbon in said titanium substrate.

8. A method of manufacturing a titanium orthopedic implant device having enhanced surface hardness and wear resistance properties, comprising the steps of:
   providing a titanium substrate in the form of an orthopedic implant device; and
   exposing said titanium substrate to an atmosphere of undiluted molecular nitrogen gas at a process temperature and for a process time duration sufficient to cause nitrogen dissolution in said titanium substrate without measurable formation of titanium nitride (TiN) on the surface of said titanium substrate, thereby enhancing the surface harness and wear resistance properties of said titanium substrate without increasing surface roughness that would diminish the wear resistance properties.

9. The method of claim 8 in which said titanium substrate comprises commercially pure titanium (CP-Titanium).

10. The method of claim 8 in which said titanium substrate comprises a titanium alloy.

11. The method of claim 10 in which said titanium alloy is Ti-5Al-4V (ELI).

12. The method of claim 8 in which said process temperature is in the range of 750° F. to 1300° F.

13. The method of claim 12 in which said process temperature is approximately 1100° F.

14. The method of claim 8 in which said process time is approximately eight hours.

15. The method of claim 8 in which said process temperature is approximately 1100° F. and said process time is approximately eight hours.

16. The method of claim 8 in which said atmosphere of molecular nitrogen gas is provided at a process pressure within the range of 1 psig to 2 psig.

17. A method of increasing the surface hardness and wear resistance properties of an orthopedic implant device that is fabricated from a titanium material, comprising the steps of:
   providing a substrate of titanium material in the form of an orthopedic implant device; and
   exposing said substrate to an atmosphere of undiluted molecular nitrogen gas at a process temperature and for a process time duration sufficient to enhance both surface hardness and wear resistance properties of said substrate by nitrogen dissolution in said substrate without increasing surface roughness and thereby diminishing wear resistance properties by the measurable formation of TiN on the surface of said substrate.

18. The method of claim 17 in which said process temperature is in the range of 750° F. to 1300° F.

* * * * *